United States Patent [19]

Odle

[11] Patent Number: 4,599,429

[45] Date of Patent: Jul. 8, 1986

[54] DESTRUCTION OF DNPI IN AN ALL NITRIC ACID NITRATION PROCESS

[75] Inventor: Roy R. Odle, Schuylerville, N.Y.

[73] Assignee: General Electric Company, Pittsfield, Mass.

[21] Appl. No.: 559,574

[22] Filed: Dec. 8, 1983

[51] Int. Cl.$^4$ ............................................. C07D 209/48
[52] U.S. Cl. ..................................... 548/481; 548/473
[58] Field of Search ................................ 548/473, 481

[56] References Cited

U.S. PATENT DOCUMENTS

| | | | |
|---|---|---|---|
| 3,868,389 | 2/1975 | Takekoshi | 260/326 N |
| 3,920,697 | 11/1975 | Takekoshi | 260/326 N |
| 3,933,852 | 1/1976 | Cook et al. | 260/326 N |
| 3,981,933 | 9/1976 | Cook et al. | 568/935 |
| 4,005,102 | 1/1977 | Cook et al. | 548/481 |
| 4,020,089 | 4/1977 | Markezich | 548/480 |

OTHER PUBLICATIONS

March, Jerry, *Advanced Organic Chemistry* 2nd, McGraw-Hill, New York, (1977) pp. 388, 389, 474–476.

Blatt, A. H. Ed. "Organic Syntheses: Collective Volume 2", John Wiley & Sons, Inc., N.Y., N.Y. p. 459, 1943.

Kirk–Othmer Encyclopedia of Chemical Technology, John Wiley & Sons, Inc. 1981.

*Primary Examiner*—Donald G. Daus
*Assistant Examiner*—G. Hendricks
*Attorney, Agent, or Firm*—Edward K. Welch, II; William F. Mufatti; John W. Harbour

[57] ABSTRACT

A means for decomposing undesirable by-products formed during the nitration by nitric acid only of N—$C_1$ to $C_8$ alkyl phthalimides which comprises elevating the temperature of the reaction mix during or following nitration and an improved nitration process incorporating said means.

22 Claims, No Drawings

DESTRUCTION OF DNPI IN AN ALL NITRIC ACID NITRATION PROCESS

The present invention is concerned with a means for decomposing di-nitro by-products derived from the organic starting reactant in a nitration process which employs nitric acid only and, more importantly, an improved process for preparing nitrated derivatives of N-alkylphthalimide by incorporating therein the foregoing means. Specifically, di-nitro derivative by-products of the organic reactant in a nitration process which employs only nitric acid may be decomposed by elevating the temperature of the reaction mix, during or following nitration, to a temperature of at least 40° C., preferably from about 50° C. to about 60° C. More specifically, in a nitration process which employs only nitric acid wherein a solution of N-alkylphthalimide is nitrated in a solvent of nitric acid of at least about 95% by weight concentration, preferably at least about 97.5% by weight concentration, the present invention provides for an improvement comprising the additional step of elevating the temperature of the reaction mix to at least about 40° C., preferably from about 50° C. to about 60° C. prior to work-up for recovering the product.

Alternative methods for preparing N-alkyl nitrophthalimides are constantly being sought as these compounds are especially useful as basic starting reactants for making a variety of organic dianhydrides and polyimides as shown by Heath et al, U.S. Pat. Nos. 3,879,428; 3,847,867 and 3,787,475, all assigned to the same assignee as the present invention.

Prior to the present invention one method for preparing N-substituted nitrophthalimides involved effecting a reaction between nitrophthalic anhydride and an organic isocyanate in the presence of an alkali carbonate catalyst. See e.g. Takekoshi, U.S. Pat. No. 3,868,389. Another method for the preparation of N-alkyl nitrophthalimides was disclosed by Cook et al, U.S. Pat. No. 3,933,852, wherein a solution is prepared of N-alkylphthalimide in a solvent composed of 98–103% by weight concentrated sulfuric acid, contacting said solution with a 98–100% by weight concentrated nitric acid within a temperature range of 60° to 80° C. and thereafter recovering the reaction product by methylene chloride extraction.

More recently, co-pending patent application Ser. No. 559,616 filed Dec. 8, 1983, incorporated herein by reference, discloses a nitric acid only process (i.e. all nitric acid nitration process) for the nitration of N-alkylphthalimide to form N-alkyl nitrophthalimides. Generally, the specification discloses a method for making N-alkyl nitrophthalimides of the formula

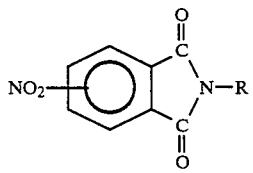

wherein R is an alkyl group having from 1 to 8, preferably from 1 to 4, carbon atoms, which comprises mixing N-alkylphthalimide with at least about 95% by weight, preferably at least about 97.5 by weight concentrated nitric acid; reacting the mixture within a temperature range of approximately, −20° C. to the boiling point of the nitric acid used, preferably from about 20° C. to about 60° C.; allowing the reaction to run and thereafter recovering the nitrated products by known methods to obtain a mixture composed essentially of the 3- and 4-isomers of N-alkyl nitrophthalimide. The weight ratio of the starting reactants, nitric acid to N-alkylphthalimide is from about 0.4 to about 50, preferably from about 5 to about 30, most preferably from about 9 to about 15.

It has recently been discovered, however, that during the all nitric acid nitration process of N-alkylphthalimide, in addition to the 3- and 4-isomers of N-alkyl nitrophthalimide, a minor amount of di-nitro derivatives of the N-alkylphthalimide, primarily consisting of the compound 3,5-di-nitro-4-hydroxy-N alkyl phthalimide (DNPI), is formed as undesirable by product. The amount of DNPI present in the reaction product may vary from about 1 to about 3% by wt. based on the products, depending upon the period of time and the temperature at which the reaction is run. The DNPI is undesirable due to its detrimental effect on subsequent nitro displacement reactions in forming higher polymers and discoloration of said polymers.

SUMMARY

A means has now been discovered by which di-nitro by-products formed during the nitration process which employs nitric acid only may be decomposed, said means comprising elevating the temperature of the reaction mix during or following nitration to a temperature of at least about 40° C., preferably from about 50° C. to about 60° C.

Additionally, the present invention provides for an improved nitration process which employs nitric acid only for the preparation of N-alkyl nitrophthalimides wherein the improvement comprises incorporating said means into the nitration process before work-up of the reaction mix prior to recovery of the nitration products.

More specifically, the improved all nitric acid nitration process comprises (1) forming a solution of N-alkylphthalimide in a solvent of nitric acid of at least about 95% by weight concentration, preferably at least about 97.5% by weight concentration, (2) allowing the nitration to proceed and (3) thereafter elevating the temperature of the reaction mix to at least 40° C., preferably from about 50° C. to about 60° C. prior to work-up for recovery of the products. The nitrated products may be recovered by known methods to obtain a mixture essentially comprising the 3- and 4- isomers of N-alkyl nitrophthalimide and which is substantially free of DNPI.

The point in time and the length of time for which the reaction mixture should be subjected to the elevated temperatures are not critical. One preferred method is where at least about 75% of the N-alkylphthalimide has reacted prior to elevating the temperature and the reaction mixture is subject to the elevated temperature for sufficient period of time to allow for the destruction of the DNPI, preferably at least about 30 minutes. Alternatively, the reaction mix may be subject to the higher temperatures upon commencing nitration and maintained throughout the nitration or after nitration is complete.

DETAILED DESCRIPTION OF THE INVENTION

For the purpose of this specification and the appended claims, the "boiling point of nitric acid" is defined as the temperature at which the specific nitric acid used, under the pressure employed, boils. This definition is necessitated by the fact that nitric acids of less then 100% concentration have a higher boiling point than 100% concentrated nitric acid and that the boiling point of nitric acid may be elevated by raising the pressure under which the reaction takes place above atmosphere. Such instances are clearly intended to be within the full scope of the present invention as set forth in this specification and claimed by the appended claims.

In a nitration process which employs only nitric acid a means has been discovered by which di-nitro by-products formed during the nitration process may be essentially eliminated. Specifically, di-nitro by-products may be decomposed into water soluble components by elevating the temperature of the reaction mix during nitration or following nitration, prior to product recovery to a temperature of from about 40° C. to the boiling point of nitric acid, preferably from about 50° C. to about 60° C. Lower temperatures will also decompose the di-nitro by-products, however, the rate is too slow and the efficiency unacceptable to be cost effective. Further, higher temperatures are effective for decomposing said di-nitro by-products and will provide somewhat higher rates of decomposition, but the time for heating and cooling and the energy costs involved, as well as the potential loss of nitric acid due to boiling make this less desirable. The means of the present invention is especially suitable for the all nitric acid nitration of N-alkylphthalimide wherein 3,5 di-nitro-4-hydroxyalkylphthalimide is formed as the primary by-product.

Incorporation of the aforementioned means into the nitration process which employs only nitric acid results in an improved nitration process whereby the nitrated products are essentially free of di-nitro by-products.

In general, the improved nitration process which employs nitric acid only is run as disclosed in the aforementioned copending patent application, subject to the same variables and parameters discussed therein, as reiterated below, except that during the nitration process or following nitration, prior to product work-up for recovery, the temperature of the reaction mix is elevated to a temperature of from about 40° C. to the boiling point of nitric acid, preferably from about 50° C. to about 60° C.

Inasmuch as the aforementioned application discloses and claims a nitration process which employs nitric acid and which may be run at temperatures greater than 40° C., thus it has now been found, destroying some or most all di-nitro by-products, this additional step is not necessary. However, by elevating the temperature of the reaction mix even higher, yields of greater purity with much less discoloration would result. Generally, however, the present process is directed more appropriately to nitration processes conducted at temperatures of about 50° C. and below, most appropriately about 40° C. and below.

Specifically, the improved nitration process which employs nitric acid only should employ nitric acids having a concentration of at least about 95% by weight and is preferably within the range of from about 97.5 to about 100% by weight concentration. Nitric acids of lower concentration are useful for the nitration process; however, the use of such lower concentration results in processes that are too slow to be cost effective. Nitric acids of such concentrations are available commercially or may be prepared by known concentrating methods from more widely available commercial nitric acid of 60 to 67% by weight concentration.

The amount of concentrated nitric acid used should be at least of the stoichiometric amount necessary to attach one $NO_2$ group on the aromatic nucleus of the N-alkylphthalimide. Generally, the weight ratio of nitric acid to the N-alkylphthalimide should be from about 0.4 to about 50, preferably from about 5 to about 30, most preferably from about 9 to about 15. Lower amounts of nitric acid result in poor yields and too slow a reaction rate as to be cost effective, whereas higher amounts of nitric acid may result in unnecessary spoiling of concentrated nitric acid and increased cost for such acid and its recycling.

The N-alkylphthalimides suitable for the nitration process disclosed herein are those of the formula

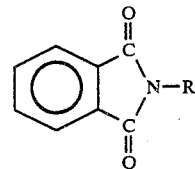

wherein R is a $C_1$ to $C_8$, preferably $C_1$ to $C_4$, hydrocarbon. They may be prepared by effecting reaction between an alkylamine and phthalic anhydride as taught by Markezich in U.S. Pat. No. 4,020,089, incorporated herein by reference. The N-alkylphthalimide may be added to the reactor in any suitable form, e.g. powder, flake, etc. This process is particularly suitable for the nitration of N-alkylphthalimide wherein the alkyl group is methyl, ethyl, n-propyl, i-propyl or n-butyl.

The improved process of the present invention comprises mixing together the concentrated nitric acid and the N-alkylphthalimide in a reactor equipped with a stirrer or agitating means and means for heating or cooling the reactor; allowing the reaction to proceed and thereafter elevating the temperature of the reaction mixture to at least about 40° C., preferably from about 50° C. to about 60° C. prior to work-up for recovery of the nitration products. The reaction products themselves, may be recovered from the reaction mix by any of the known methods for recovery of nitrated products.

As mentioned above, the temperature at which the nitration process should run is not critical insofar as the nitration itself is concerned. The actual temperature to be employed is dependent upon the desired rate of reaction and the desired end products. In general, the lower the temperature the slower the reaction and the greater the ratio of the 4- isomer to 3- isomer formed in the products. Conversely, with the higher temperatures, the reaction rate is increased and the ratio of 4- isomer to 3- isomer is smaller.

While the temperature at which the reaction is run has the most significant impact on reaction rate, the specific reactants used and the ratio of reactants in the reaction mix also greatly influence the reaction rate. With respect to the former, the higher the concentration of the nitric acid in the initial mix or as added during continuous processing the faster the reaction rate. Further, the specific alkyl group on the N-alkylphthalimide is found to influence reaction rate. Generally, it has been found that the more electron donating alkyl groups, especially for example isopropyl, influence a comparatively faster reaction than for example, the methyl group.

Finally, with respect to the ratio of the reactant mix, it is found that the rate of reaction increases as the ratio of nitric acid to N-alkylphthalimide increases. The most dramatic increase, in this respect, being noted as the reactant ratio approaches about 10.

Thus by varying any one or all of the foregoing, one may significantly increase or decrease the time for which the reaction should run to obtain optimum yield.

When the nitration process is run without the improvement of the present invention, the reaction products are comprised primarily of 3- and 4- isomers of the respective N-alkyl nitrophthalimide; however, they also contain undesirable by-products, particulary the compound 3,5-di-nitro-4-hydroxy-N-alkylphthalimide (DNPI), and are found to have a distinct yellow discoloration. The DNPI formed may be present in an amount up to about 3% by wt. based on the products. The specific amount depending upon the reaction conditions.

Specifically, although higher initial levels of DNPI are formed with higher reaction temperatures, the rate of destruction of DNPI increases as the temperature increases such that reactions run at higher temperatures have a lower level of DNPI in the final product than reactions run at lower temperatures. Similarly, the ratio of reactants in the reaction mix also influences the level of DNPI. Once again higher ratios of nitric acid to N-alkylphthalimide result in an initial higher level of formation of DNPI with a subsequent greater rate of destruction. Thus DNPI may be avoided or mitigated by running the nitration at higher temperatures or by using a high weight ratio of starting reactants. Even so, the nitration products may contain up to about 3% of DNPI.

In accordance with the present invention, DNPI formed in the reaction mixture is destroyed by the additional step of elevating the temperature of the reaction mixture to a temperature of at least 40° C., preferably from about 50° C. to about 60° C., during or following nitration, prior to work-up fo recovery of the products. The period of time for which the reaction product mixture should be subjected to this elevated temperature is not critical since DNPI breakdown is continuous. However, in order to be assured that most DNPI is destroyed, it is preferred that the reaction product be subjected to these elevated temperatures for at least 30 minutes, preferably from about 30 minutes to 120 minutes.

The time at which the reaction mixture is elevated to at least 40° is also not critical, however, it is preferred that the reaction have been allowed to progress to the point where at least about 75% of the N-alkylphthalimide is nitrated, approximately 2.5 hours when reaction parameters are in the preferred ranges. Alternatively, the reaction may be allowed to run until it is essentially completed, approximately 3 hours or more, and then the temperature elevated so as to destroy the DNPI.

After the reaction product mix has been subjected to the higher temperatures for a sufficient period of time to allow for the destruction of the DNPI, the reaction products may then be recovered from the reaction mix by any of the known methods of recovery of nitrated products. Exemplary of the methods available include: extraction; spray drying; precipitation and drying and the like. The decomposition products of the DNPI are water soluble such that they are easily washed from the reaction product mix to give a very pure mixture of 3- and 4- Nitro-N-alkylphthalimide having less than about 0.3% by weight, preferably less than about 0.1% by weight, of DNPI and only a faint, if any, yellow tint.

The foregoing reaction process is suitable for use in either batch processing or continuous reaction processes.

Specific variations in the design of the process systems employable to practice the present invention are known to those skilled in the art. For example, it is possible to use one or more reactors in series or in parallel which operate in the plug flow mode with or without radial mixing and with or without heating or cooling. Alternatively, it is possible to use one or more reactors in series or in parallel The mode of mixing and sequence of addition of reactants is not critical to the present invention. Feed of the reactants may either be into the first reactor or be portioned among the reactors if more than one reactor is used, or they may be entered at different locations of the reactor or reactors. Further, the reactants may be pre-mixed before entering the reaction process or they may be fed separately. It is also possible that one or both reactants are brought to the desired reaction temperature prior to mixing or entering the reactor.

The pressure range under which this process operates may vary from vacuum to above atmospheric pressure. Depending on the type of reactor or reactors employed, they may preferentially operate under slight vacuum for process and safety reasons. Otherwise, the process is generally run at about atmospheric pressure.

In order that those skilled in the art may better understand how the present invention may be practiced, the following examples are given by way of illustration and not by way of limitation.

DESCRIPTION OF THE PREFERRED EMBODIMENTS

Generally, reaction products were analyzed by High Pressure Liquid Chromatography (HPLC) wherein 50 μl aliquots were quenched into 3 mls of an aqueous phase and 2 mls of an organic phase: the former comprising 0.1 M tetramethylammonium chloride in water and 1.0% methanol and the latter comprising 10% methanol in acetonitrile. The samples were analyzed at 280 nm on a DuPont ODS-RP column using 1.5 ml/min of mobile phase. A solvent gradient of 12–40% organic phase was programmed using a linear gradient over 20 minutes.

EXAMPLE E1, COMPARATIVE EXAMPLE CE1

Two reactions were run wherein 10 parts by wt. N-methylphthalimide was dissolved in 100 parts by wt. of 99.7% nitric acid at 40° C. after two hours at 40° C. the reaction mixture of example E1 was elevated to 50° C. while comparative example CE1 was maintained at 40° C. The reaction was allowed to run for another hour, after which both reaction mixtures were analyzed. Both E1 and CE1 were comprised essentially of a mixture of the 3- and 4- isomer of Nitro-N-methyl-phthalimide. However, CE1 contained about 1.85% by wt. of 3,5 di-nitro-4-hydroxy-N-methyl-phthalimide as compared to about 0.06% by wt. in example E1. Further CE1 had a distinct yellow discoloration, whereas the compounds produced by the present invention had only a faint yellow tint.

EXAMPLE E2, COMPARATIVE EXAMPLE CE2

10 parts by wt. N-methyl-phthalimide was dissolved in 100 parts by wt. of 99% nitric acid at 30° C. The nitration reaction was allowed to proceed at 30° C. for 120 minutes after which one-half of the reaction mixture was withdrawn from the reaction vessel and placed in a separate vessel at 60° C. (Example E2). The remaining reaction mixture was allowed to proceed at 30° C. (Comparative Example CE2). At that time, the reaction mixture E2 and CE2 contained 1.77% by wt. 3,5 di-nitro-4-hydroxy-N-methyl-phthalimide. At 150 minutes, 30 minutes after splitting, 3,5 di-nitro-4-hydroxy-N-methyl-phthalimide in E2 was reduced to 0.26% by wt. whereas, 3,5 di-nitro-4-hydroxy-N-methyl-phthalimide in CE2 was 1.59% by wt. Finally, after 180 minutes, 60 minutes from splitting, the amount of 3,5 di-nitro-4-hydroxy-N-methyl-phthalimide in E2 and CE2 was 0.12 and 1.54% by wt., respectively.

Additionally, elevating the temperature also speeded the nitration reaction to completion. After 180 minutes, total elapsed time, only 0.54% by wt. of N-methyl-phthalimide remained unreacted in E2 as compared to 9.30% by wt. in CE2.

Obviously, other modifications and variations of the present invention are possible in light of the above teachings. It is, therefore, to be understood that changes may be made in the particular embodiments of the invention described which are within the full intended scope of the invention as defined by the appended claims.

I claim:

1. A means of decomposing undesirable by-products formed during the nitration by nitric acid only of N-$C_1$ to $C_8$ alkyl phthalimides, said means comprising elevating the temperature of the reaction mix after the onset of nitration or following nitration to at least about 40° C. and maintaining said elevated temperature until nitration is complete and/or substantially all by-product is decomposed.

2. The means of claim 1 wherein the temperature is elevated after the onset of nitration.

3. The means of claim 1 wherein the temperature is elevated once the nitration process is substantially complete.

4. The means of claim 1 wherein the temperature is elevated after the nitration is completed, just prior to product recovery.

5. The means of claim 1 wherein the temperature is elevated to from about 50° C. to about 60° C.

6. The means of claim 1 wherein the temperature is elevated for at least about 30 minutes.

7. The means of claim 1 wherein the temperature is elevated for from about 30 minutes to about 120 minutes.

8. The means of claim 1 wherein the organic reactant is N-methylphthalimide and the undesirable by-product is 3,5-di-nitro-4-hydroxy-N-methylphthalimide.

9. The improved process for obtaining nitrated derivatives of N-$C_1$ to $C_8$ alkylphthalimide wherein nitric acid is both solvent and nitrating agent which comprises mixing the N-alkylphthalimide with a nitric acid of at least about 95% by weight concentration in a weight ratio of the latter to the former of from about 0.4 to about 50, allowing the reaction to run and thereafter recovering the nitrated products to obtain a mixture composed essentially of M-alkyl 3-nitrophthalimide and N-alkyl 4-nitrophthalimide wherein the improvement comprises the additional step of elevating the temperature of the reaction mixture to a temperature of from about 40° C. to the boiling point of nitric acid after the onset of nitration or following nitration for a sufficient period of time to decompose undesirable by-products prior to recovery of the reaction product.

10. The process of claim 9 wherein the temperature of the reaction mixture is elevated to at least about 40° C. prior to product recovery.

11. The process of claim 9 wherein the temperature of the reaction mixture is elevated to a temperature of from about 50° C. to about 60° C. prior to recovery of the reaction product.

12. The process of claim 9 wherein the temperature of the reaction mixture is elevated for a period of at least 30 minutes.

13. The process of claim 9 wherein the temperature of the reaction mixture is elevated for a period of from about 30 minutes to about 120 minutes.

14. The process of claim 9 wherein the nitric acid is from about 97.5 to about 100% by weight concentration.

15. The process of claim 9 wherein the weight ratio of nitric acid to N-alkylphthalimide is from about 0.4 to about 50.

16. The process of claim 9 wherein the weight ratio of nitric acid to N-alkylphthalimide is from about 5 to about 30.

17. The process of claim 9 wherein the weight ratio of nitric acid to N-alkylphthalimide is from about 9 to about 15.

18. The process of claim 9 wherein the temperature range of the nitration process is from about 20° C. to about 50° C.

19. The process of claim 9 wherein the temperature of the reaction mixture is elevated once the nitration process is substantially completed.

20. The process of claim 9 wherein the alkyl group of the N-alkylphthalimide has from 1 to about 4 carbon atoms.

21. The process of claim 9 wherein the N-alkylphthalimide is N-methylphthalimide and the undesirable by-product is 3,5-di-nitro-4-hydroxy-N-methylphthalimide.

22. The process of claim 9 wherein the temperature is elevated following the nitration.

* * * * *